(12) United States Patent
Bonrath et al.

(10) Patent No.: US 7,622,591 B2
(45) Date of Patent: Nov. 24, 2009

(54) ROUTE TO α-TOCOPHERYL ALKANOATES AND PERCURSORS THEREOF

(75) Inventors: Werner Bonrath, Freiburg (DE); Manfred Breuninger, Bad Säckingen (DE); Grégory Malaisé, Saint-Louis (FR); Thomas Netscher, Bad Krozingen (DE)

(73) Assignee: DSM IP Assets B.V., Heerlen (NL)

( * ) Notice: Subject to any disclaimer, the term of this patent is extended or adjusted under 35 U.S.C. 154(b) by 402 days.

(21) Appl. No.: 10/571,261

(22) PCT Filed: Sep. 2, 2004

(86) PCT No.: PCT/EP2004/009749

§ 371 (c)(1), (2), (4) Date: Apr. 13, 2006

(87) PCT Pub. No.: WO2005/026142

PCT Pub. Date: Mar. 24, 2005

(65) Prior Publication Data

US 2007/0032667 A1    Feb. 8, 2007

(30) Foreign Application Priority Data

Sep. 15, 2003  (EP) .................................. 03020875

(51) Int. Cl.
C07F 15/00  (2006.01)
C07D 311/02  (2006.01)

(52) U.S. Cl. ....................................... 548/103; 549/411

(58) Field of Classification Search ................. 548/103; 549/411

See application file for complete search history.

(56) References Cited

U.S. PATENT DOCUMENTS 4,689,427 A * 8/1987 Imfeld ........................ 560/144

FOREIGN PATENT DOCUMENTS

| EP | 0 087 576 | 9/1983 |
|----|-----------|--------|
| EP | 0 183 042 | 6/1986 |
| WO | WO 03/037883 | 5/2003 |
| WO | WO 2004/046126 | 6/2004 |
| WO | WO 2004/063182 | 7/2004 |

OTHER PUBLICATIONS

Malaise et al. "A New Route to Vitamin E Key-Intermediates by Olefin Cross-Metathesis" Helvetica Chimica Acta, 2006, vol. 89, pp. 797-812.*

* cited by examiner

*Primary Examiner*—Rei-Tsang Shiao
*Assistant Examiner*—Joseph R Kosack
(74) *Attorney, Agent, or Firm*—Nixon & Vanderhye P.C.

(57) ABSTRACT

The present invention is concerned with a novel process for the manufacture of 4alkanoyloxy-2,3,5-trimethylphenyl (E/Z)-phytyl ethers, precursors of α-tocopheryl alkanoates, by cross-metathesis reaction of alkenyl ethers of 1-alkanoyloxy-2,3,6-trimethylhydroquinone with 2,6,10,14-tetramethylpentadecene or a phytol derivative, e.g. an ester, an ether or a silyl ether, in the presence of a cross-metathesis catalyst. As the crossmetathesis catalyst especially ruthenium metal carbene complexes are suitable which possess (a) ruthenium metal center(s), have an electron count of 16 or 18 and are penta- or hexa-coordinated. A further object of the invention is a process for the manufacture of αtocopheryl alkanoates comprising this reaction.

23 Claims, 5 Drawing Sheets

R = C(H)(CH$_3$)$_2$

R = C(H)(CH$_3$)$_2$

R = C(H)(CH$_3$)$_2$

ROUTE TO α-TOCOPHERYL ALKANOATES AND PERCURSORS THEREOF

This application is the US national phase of international application PCT/EP2004/009749 filed 2 Sep. 2004 which designated the U.S. and claims benefit of EP 03020875.5, dated 15 Sep. 2003, the entire content of which is hereby incorporated by reference.

The present invention is concerned with a novel process for the manufacture of 4-alkanoyloxy-2,3,5-trimethylphenyl (E/Z)-phytyl ethers, precursors of α-tocopheryl alkanoates, by cross-metathesis reaction of alkenyl ethers of 2,3,6-trimethylhydroquinone 1-alkanoate (=4-alkanoyloxy-2,3,5-trimethylphenol) with 2,6,10,14-tetramethylpentadecene or a phytol derivative, e.g. phytyl acetate, in the presence of a cross-metathesis catalyst. A further object of the invention is a process for the manufacture of α-tocopheryl alkanoates comprising this reaction step.

As is known, (all-rac)-α-tocopherol (or as it has mostly been denoted in the prior art, "d,l-α-tocopherol") is a diastereoisomeric mixture of 2,5,7,8-tetramethyl-2-(4',8',12'-trimethyltridecyl)-6-chromanol (α-tocopherol), which is the most biologically active and industrially most important member of the vitamin E group. Often the acetate of α-tocopherol is produced since it is more stable and more convenient to handle in contrast to α-tocopherol which is labile against oxidative conditions.

Many processes for the manufacture of "d,l-α-tocopherol" (referred to as such in the literature reviewed hereinafter) and its acetate are described in literature, of which some examples are discussed below. They all have in common that α-tocopherol or its acetate are produced by the reaction of trimethylhydroquinone (TMHQ)/trimethylhydroquinone acetate (TMHQA) with isophytol (IP), phytol (PH) or its derivatives in the presence of a catalyst or catalyst system and in a solvent or solvent system.

According to EP 0 100 471 e.g. the reaction of TMHQ with IP or PH is carried out in the presence of a Lewis acid, e.g. $ZnCl_2$, $BF_3$ or $AlCl_3$, a strong acid, e.g. HCl, and an amine or an amine salt of a non-oxidizing protic acid as the catalyst system.

EP-A 0 658 552 discloses a process for the preparation of α-tocopherol and derivatives thereof, wherein fluorosulfonates $[M(RSO_3)_3]$, nitrates $[M(NO_3)_3]$ and sulfates $[M_2(SO_4)_3]$ are used as the catalysts with M representing a Sc, Y or lanthanide atom, and R representing fluorine, a fluorinated lower alkyl or an optionally single or multiple fluorinated aryl. The reaction is carried out in a solvent which is inert to the catalyst and the starting materials, TMHQ and allyl alcohol derivatives or alkenyl alcohols, examples of the solvent being aromatic hydrocarbons, linear and cyclic ethers, esters and chlorinated hydrocarbons.

According to EP-B 0 694 541 a carbonate ester, a lower fatty acid ester or a mixed solvent of a non-polar solvent and a lower $C_{1-5}$-alcohol is used as solvent for the preparation of α-tocopherol starting with TMHQ and (iso)phytol or phytol derivatives. As the catalyst a mineral acid, a Lewis acid, an acidic ion exchange resin or a triflate, nitrate or sulfate of Sc, Y or a lanthanid element is used.

In the process of EP-A 1 180 517 TMHQ and IP or PH are reacted in the presence of a bis-(perfluorinated hydrocarbyl sulphonyl)imide or a metal salt thereof to obtain α-tocopherol. Solvents for this reaction are polar organic solvents such as aliphatic and cyclic ketones, aliphatic and cyclic esters and carbonates, and non-polar organic solvents such as aliphatic and aromatic hydrocarbons or mixtures thereof.

The reaction of TMHQ/TMHQA with isophytol, phytol or an (iso)phytol derivative has the disadvantage of the formation of by-products such as benzofurans and phytadienes. The separation of these by-products from α-tocopherol and its acetate, respectively, is rather difficult.

The object of the present invention is to provide a process for the manufacture of (all-rac)-α-tocopheryl alkanoates, which are stable against oxidative conditions, and precursors thereof, whereby the production of benzofurans and phytadienes is avoided. Furthermore the catalyst used should have no, or at least a much reduced, corrosive action.

One aspect of the present invention is a process for the manufacture of compounds represented by the following formula III, so called 4-alkanoyloxy-2,3,5-trimethylphenyl (E/Z)-3,7,11,15-tetramethyl-2-hexadecenyl ether (=4-alkanoyloxy-2,3,5-trimethylphenyl (E/Z)-phytyl ether; (E/Z)-4-O-phytyl 2,3,6-trimethylhydroquinone 1-alkanoate),

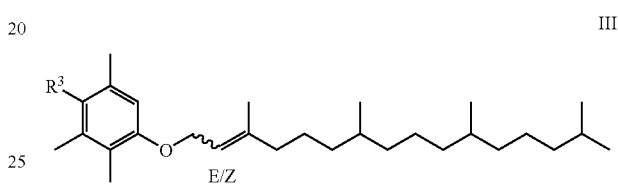

III with $R^3$ being as defined below,
by reacting
a) a compound represented by the following formula I, so-called alkenyl ethers of 2,3,6-trimethylhydroquinone 1-alkanoate,

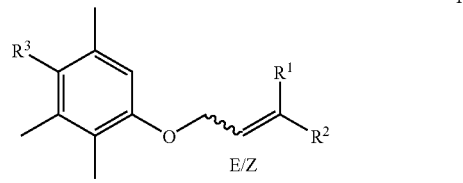

I wherein $R^1$ and $R^2$ are independently from each other H or $C_{1-5}$-alkyl, with the proviso that at least one of $R^1$ and $R^2$ is not H, and wherein $R^3$ is $C_{2-5}$-alkanoyloxy, with
b) a compound represented by the following formula II, 2,6,10,14-tetramethylpentadecene (if $R^4$=H) or a phytol derivative (if $R^4$=$CH_2R^5$),

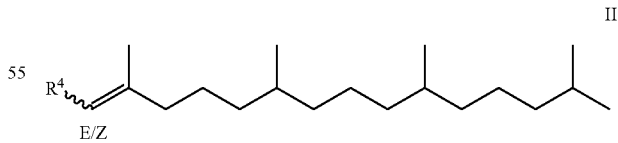

II wherein $R^4$ is H or $CH_2R^5$, wherein $R^5$ is formyloxy, $C_{2-5}$-alkanoyloxy, benzoyloxy, $C_{1-5}$-alkoxy, or $OSiR^6R^7R^8$, wherein $R^6$, $R^7$ and $R^8$ are independently from each other $C_{1-6}$-alkyl or phenyl,
in the presence of a cross-metathesis catalyst.

These so-called 4-alkanoyloxy-2,3,5-trimethylphenyl (E/Z)-phytyl ethers are 2,3,6-trimethylhydroquinone 1-alkanoate derivatives and suitable precursors for α-tocopheryl alkanoates represented by the formula V as shown in FIG. 1. The reaction of a compound of formula I with a compound of formula II is a cross-metathesis reaction. The compounds represented by formula VI (see FIG. 1) are produced as byproducts. They can easily be removed by distillation or column chromatography.

Concerning the substituents $R^1$ and $R^2$: The expression "$C_{1-5}$-alkyl" embraces linear $C_{1-5}$-alkyl and branched $C_{3-5}$-alkyl. Preferably $R^1$ and $R^2$ are independently from each other $C_{1-5}$-alkyl, more preferably they are both identical $C_{1-5}$-alkyl, most preferably they are both methyl.

Concerning the substituent $R^3$: The term "$C_{2-5}$-alkanoyloxy" covers linear $C_{2-5}$-alkanoyloxy and branched $C_{4-5}$-alkanoyloxy. $R^3$ is preferably acetyloxy or pivaloyloxy, more preferably it is acetyloxy.

Concerning the substituent $R^4$: The expression "$C_{2-5}$-alkanoyloxy" incorporates linear $C_{2-5}$-alkanoyloxy and branched $C_{4-5}$-alkanoyloxy, the expression "$C_{1-5}$-alkoxy" covers linear $C_{1-5}$-alkoxy and branched $C_{3-5}$-alkoxy, and the term $C_{1-6}$-alkyl encloses linear $C_{1-6}$-alkyl and branched $C_{3-6}$-alkyl.

$R^4$ is preferably H or $CH_2R^5$, wherein $R^5$ is formyloxy, $C_{2-5}$-alkanoyloxy, benzoyloxy and $OSiR^6R^7R^8$. Preferred examples for $OSiR^6R^7R^8$ are $OSiMe_3$, $OSi^tBuMe_2$, $OSiMe_2Ph$, $OSiEt_3$ and $OSi^iPr_3$, more preferred examples are $OSiMe_3$ and $OSi^tBuMe_2$ (Me=methyl, $^t$Bu=tert-butyl, Ph=phenyl, Et=ethyl, $^i$Pr=iso-propyl).

More preferably $R^4$ is H or $CH_2R^5$ with $R^5$ being formyloxy, $C_{2-5}$-alkanoyloxy or benzoyloxy.

THE CROSS-METATHESIS CATALYST

Figure 1:
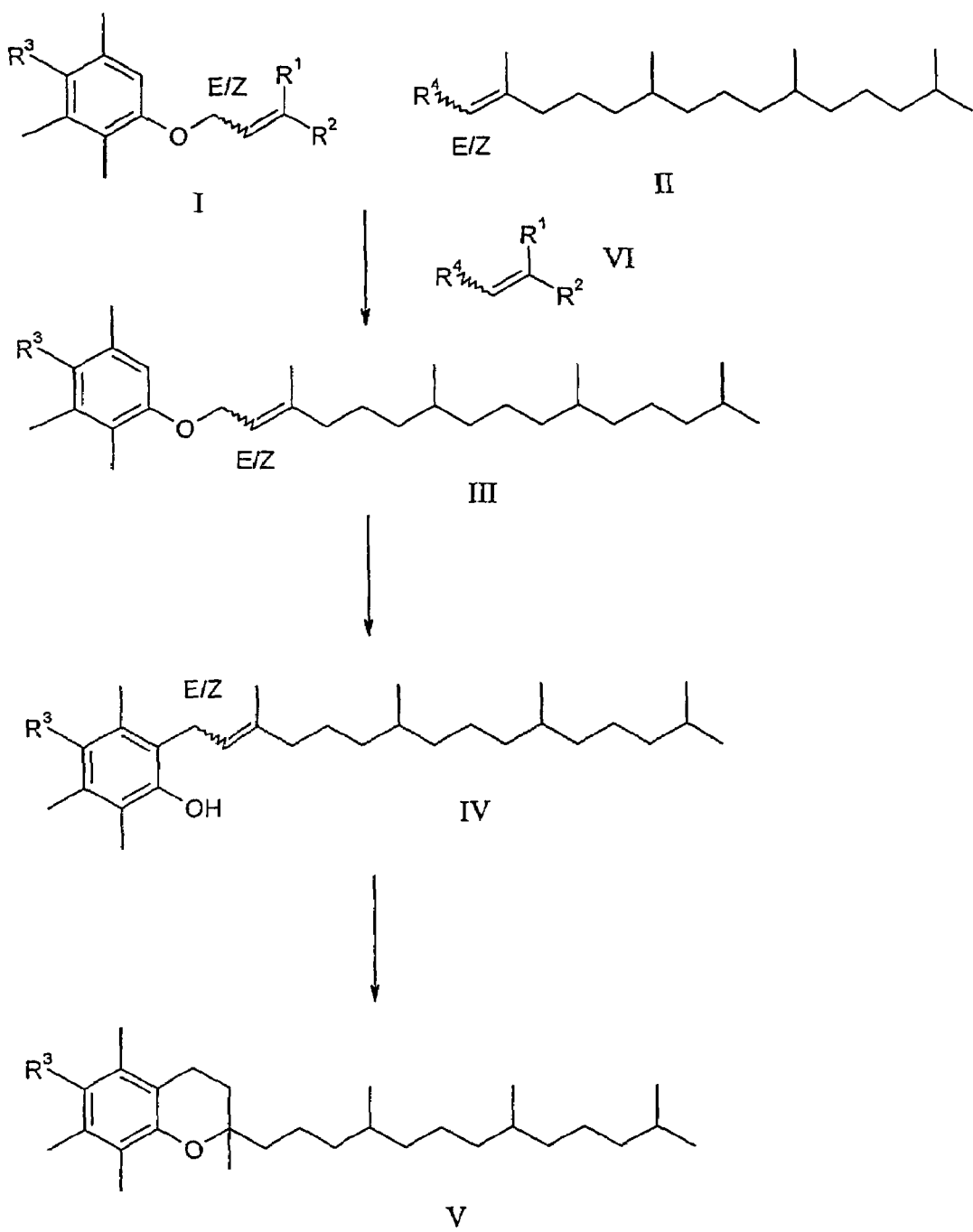
FIG. 1 depicts the structures of compounds of formula I, formula II, formula, III, formula IV, formula V, and formula VI and their relationships and the manufacture of compounds of formula V starting from compounds of formula I and II via compounds of formula III and IV.

Preferably the cross-metathesis catalyst used in the process according to the invention is a ruthenium compound used in homogeneous catalysis. Homogeneous catalysis means that the reaction mixture is monophasic during the catalyzed reaction.

More preferably the ruthenium compound is a ruthenium metal carbene complex possessing (a) ruthenium metal center(s), having an electron count of 16 and being penta-coordinated or a ruthenium metal carbene complex possessing (a) ruthenium metal center(s), having an electron count of 18 and being hexa-coordinated. Preferred is a ruthenium metal carbene complex possessing a ruthenium metal center, having an electron count of 16 and being penta-coordinated. It has to be kept in mind that these are the forms in which the catalysts are present before the reaction, so-called "precatalysts". The real "catalytic" species is formed in situ during the reaction, of which the structure is not known.

"Penta-coordinated" in this context does not necessarily mean that there are five ligands per Ru metal center in the complex. It is also possible that one ligand provides two coordination sites, i.e. that the complex contains four ligands per Ru metal center. The same applies for the term "hexa-coordinated". Hexa-coordinated Ru-complexes might contain five or six ligands, one of the five ligands providing two coordination sites, a so-called bidentate ligand.

More preferred examples for such ruthenium compounds are the ruthenium metal carbene complexes represented by the following formulae VIIa, VIIb and VIIc:

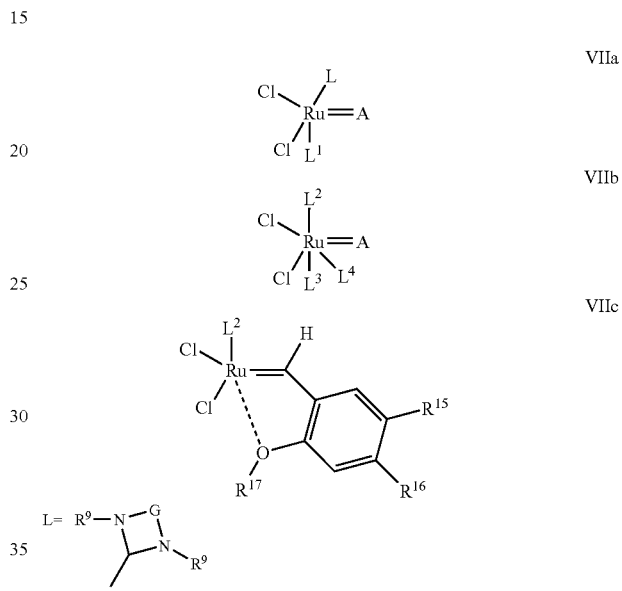

wherein $R^9$ is an optionally single or multiple $C_{1-5}$-alkylated and/or $C_{1-5}$-alkoxylated phenyl, G is ethane-1,2-diyl, ethylene-1,2-diyl, cyclohexane-1,2-diyl or 1,2-diphenylethane-1,2-diyl, $L^1$ is $PR^{10}R^{11}R^{12}$, wherein $R^{10}$, $R^{11}$ and $R^{12}$ are independently from each other $C_{1-8}$-alkyl, phenyl or tolyl, A is $CH_2$, C(H)aryl, $C(H)R^{13}$, $C=C(R^{13})_2$, C=C(H)Si$(R^{14})_3$, C(H)—C(H)=C(R$^{13}$)$_2$, C=C(H)(phenyl), C(H)—C(H)=C(phenyl)$_2$ or C=C=C(phenyl)$_2$, wherein "aryl" is an optionally single or multiple $C_{1-5}$-alkylated and/or halogenated phenyl, $R^{13}$ is $C_{1-4}$-alkyl, $R^{14}$ is $C_{1-6}$-alkyl or phenyl, $L^2$ is L or $L^1$, $L^3$ and $L^4$ are independently from each other pyridyl or 3-halopyridyl, wherein halo signifies Br or Cl, $R^{15}$ and $R^{16}$ are both H or form together a fused benzene ring, and $R^{17}$ is $C_{1-5}$-alkoxy.

Concerning the substituent $R^9$: Preferred examples for an optionally single or multiple $C_{1-5}$-alkylated and/or $C_{1-5}$-alkoxylated phenyl are phenyl, 2,6-dimethylphenyl, 2,3,6-trimethylphenyl, 2,4,6-trimethylphenyl, 2,6-dimethyl-4-methoxy-phenyl, 2-isopropylphenyl, 2,6-diisopropylphenyl and 2-isopropyl-6-methylphenyl. More preferred examples for $R^9$ are 2,6-dimethylphenyl, 2,4,6-trimethylphenyl, and 2,6-diisopropylphenyl.

Concerning the substituent G: Preferably G is ethane-1,2-diyl.

Concerning the substituent $L^1$: The term "$C_{1-8}$-alkyl" includes linear $C_{1-8}$-alkyl, branched $C_{3-8}$-alkyl and $C_{5-8}$-cycloalkyl. Preferably $L^1$ is $P(R^{10})_3$, wherein $R^{10}$ is linear $C_{1-8}$-alkyl, $C_{5-8}$-cycloalkyl or phenyl. More preferably $L^1$ is $P(C_6H_{11})_3$ ("$C_6H_{11}$"=cyclohexyl), $P(C_5H_9)_3$ ("$C_5H_9$"=cyclopentyl) or $PPh_3$ ("Ph"=phenyl).

Concerning the substituent A: The term "halogenated" means fluorinated, chlorinated or brominated, whereby chlorinated is preferred. Preferred examples for an optionally single or multiple $C_{1-5}$-alkylated and/or halogenated phenyl are phenyl, 4-chlorophenyl, 2,6-dimethylphenyl, 2,3,6-trimethylphenyl, 2,4,6-trimethylphenyl, 2,6-dimethyl-4-methoxyphenyl, 2-isopropylphenyl, 2,6-diisopropylphenyl and 2-isopropyl-6-methylphenyl. The expression "$C_{1-4}$-alkyl" (substituent $R^{13}$) includes linear $C_{1-4}$-alkyl as well as branched $C_{3-4}$-alkyl. The expression "$C_{1-6}$-alkyl" (substituent $R^{14}$) includes linear $C_{1-6}$-alkyl as well as branched $C_{3-6}$-alkyl.

Preferably A is $C(H)CH_3$, $C(H)CH_2CH_3$, $C(H)(phenyl)$, $C(H)(4\text{-chlorophenyl})$, $C=C(H)(phenyl)$, $C=C(H)Si(CH_3)_3$ and $C(H)-C(H)=C(phenyl)_2$ or $C(H)-C(H)=C(Me)_2$. More preferably A is $C(H)(phenyl)$, $C(H)-C(H)=C(phenyl)_2$ or $C(H)-C(H)=C(Me)_2$. Most preferably A is $C(H)(phenyl)$.

Concerning the substituents $L^3$ and $L^4$: Preferably $L^3$ and $L^4$ are both identical. More preferably they are both 3-bromopyridyl.

Concerning the substituents $R^{15}$ and $R^{16}$: Preferably they are both H.

Concerning the substituent $R^{17}$: The term "$C_{1-5}$-alkoxy" includes linear $C_{1-5}$-alkoxy as well as branched $C_{3-5}$-alkoxy. Preferably $R^{17}$ is isopropoxy or methoxy, more preferably $R^{17}$ is isopropoxy.

Figure 2:
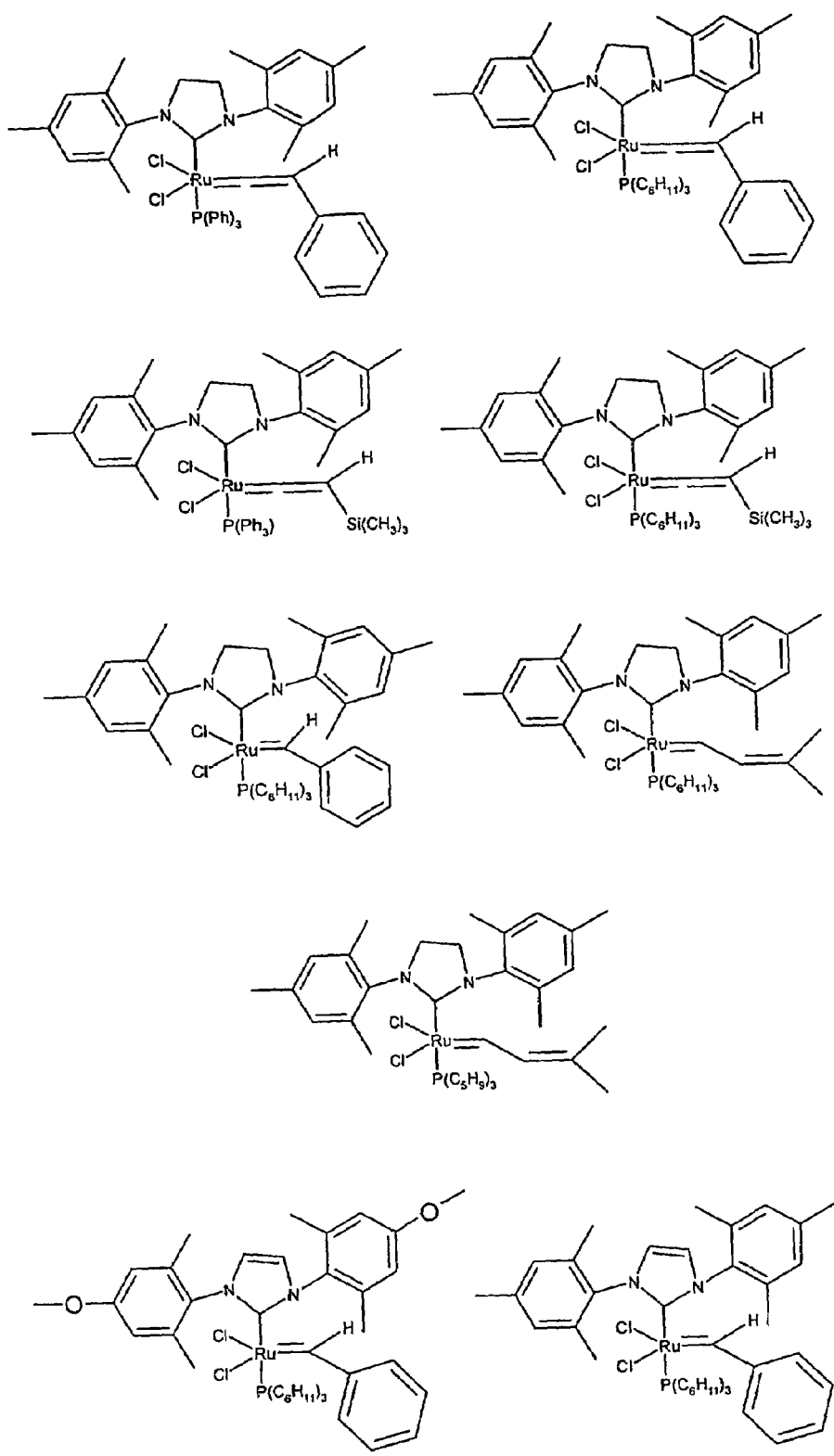
FIG. 2 depicts preferred examples for complexes represented by the formula VIIa.
Figure 3:
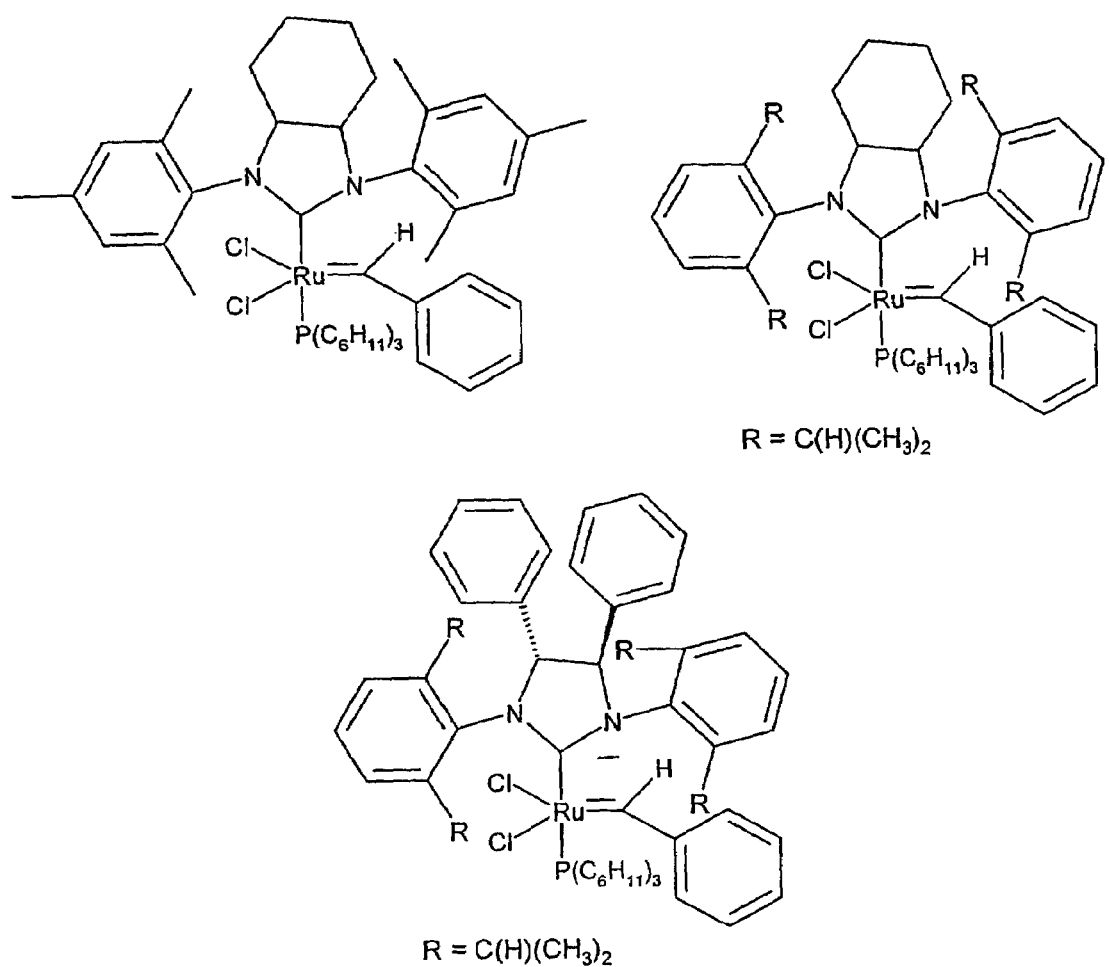
FIG. 3 depicts additional preferred examples for complexes represented by the formula VIIa.
Figure 4:
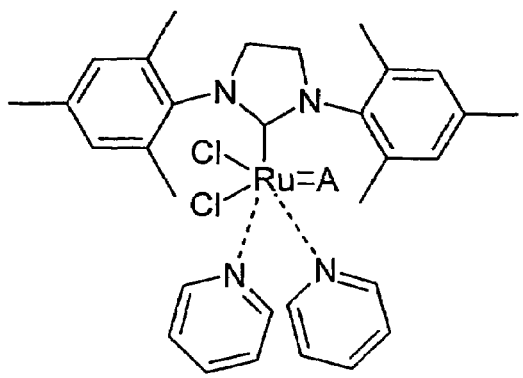
FIG. 4 depicts preferred examples for complexes represented by the formula VIIb (A is $CH_3$, $C(H)CH_3$, $C(H)CH_2CH_3$, C(H)(phenyl), C(H)(4-chlorophenyl), C=C(H)(phenyl), C=C(H)Si(CH$_3$)$_3$, C(H)—C(H)=C(phenyl)$_2$, and C(H)=C(Me)$_2$).
Figure 4:
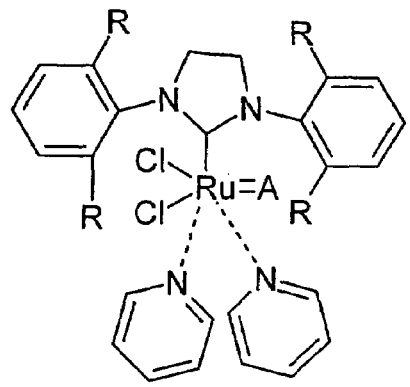
Figure 4:
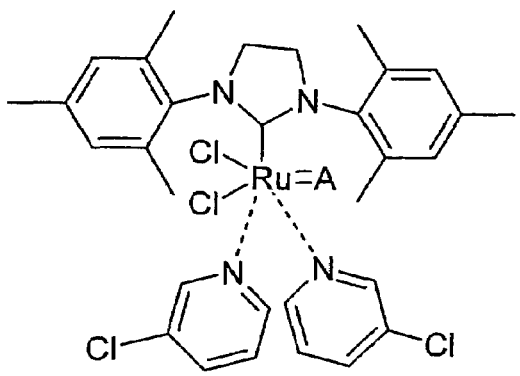
Figure 4:
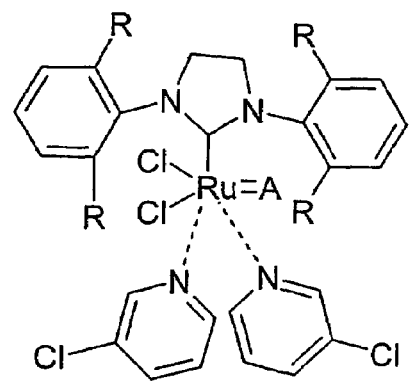
Figure 4:
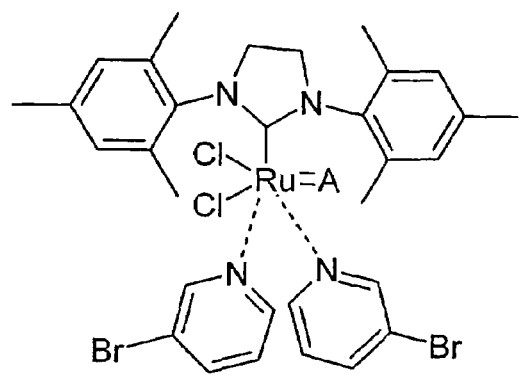
Figure 4:
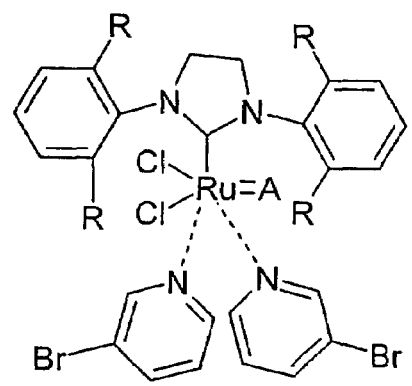
Figure 5:
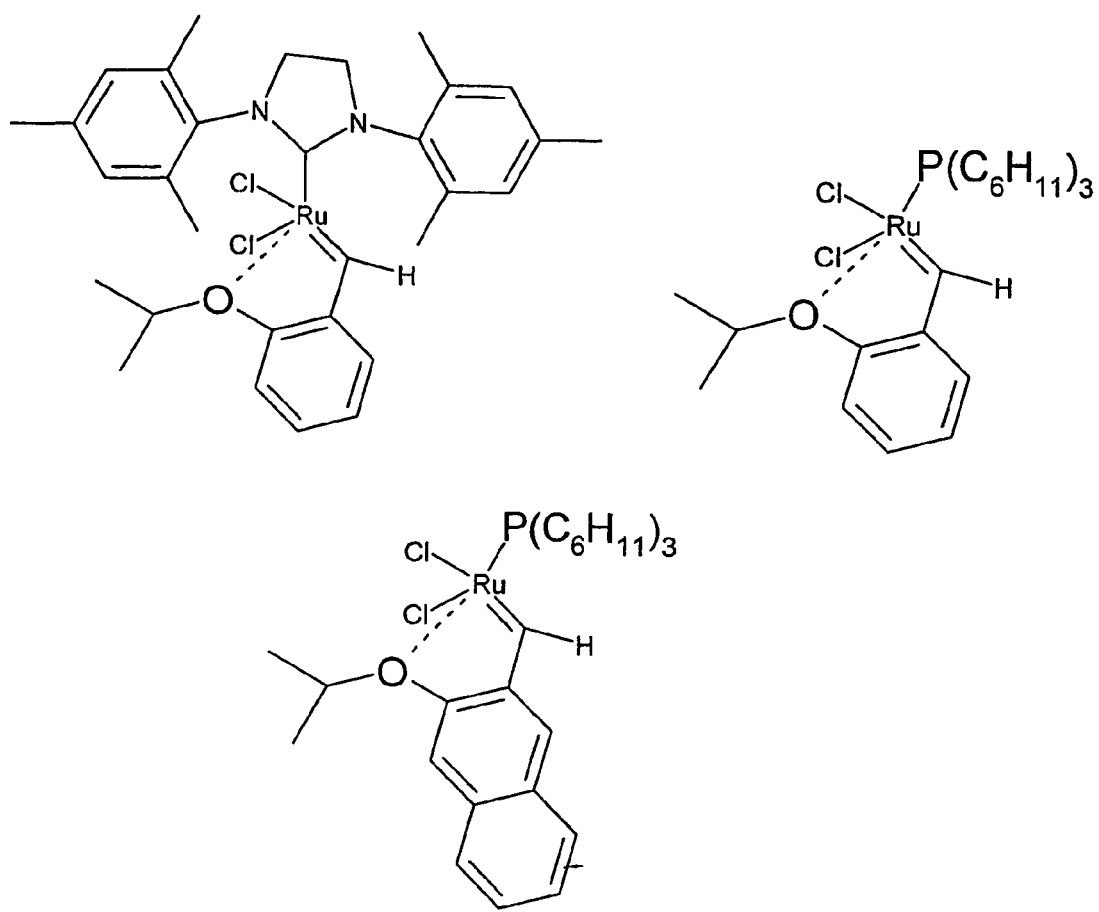
FIG. 5 depicts preferred examples for complexes represented by the formula VIIc.

Preferred examples for complexes represented by the formula VIIa are illustrated in FIGS. 2 and 3. Preferred examples for complexes represented by the formula VIIb are illustrated in FIG. 4 (A is $C(H)CH_3$, $C(H)CH_2CH_3$, $C(H)(phenyl)$, $C(H)(4\text{-chlorophenyl})$, $C=C(H)(phenyl)$, $C=C(H)Si(CH_3)_3$, $C(H)-C(H)=C(phenyl)_2$ and $C(H)-C(H)=C(Me)_2$). Preferred examples for complexes represented by the formula VIIc are illustrated in FIG. 5.

The most preferred cross-metathesis catalyst used in the process according to the invention is the following ruthenium metal carbene complex of formula VIII:

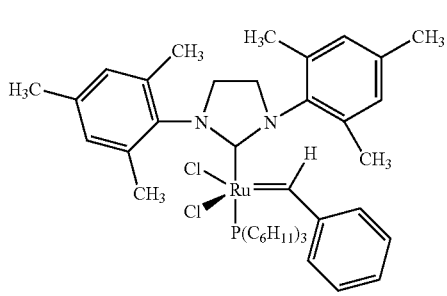

VIII

Synthesis of the Catalyst

The synthesis of the ruthenium carbene complexes represented by the formulae VIIa, VIIb, VIIc and VIII is e.g. described by P. Schwab, M. B. France, J. W. Ziller and R. H. Grubbs in Angew. Chem. Int. Ed. Engl. 1995, 34(18), 2039-2041; by M. Scholl, S. Ding, C. W. Lee and R. H. Grubbs in Organic Letters 1999, 1(6), 953-956 (see especially footnote 16); by S. B. Garber, J. S. Kingsbury, B. L. Gray and A. H. Hoveyda in J. Am. Chem. Soc. 2000, 122, 8168-8179; by J. Huang, E. D. Stevens, S. P. Nolan and J. L. Petersen in J. Am. Chem. Soc. 1999, 121, 2674-2678 (see especially page 2678); by M. Scholl, T. M. Trnka, J. P. Morgan and R. H. Grubbs in Tetrahedron. Lett. 1999, 40, 2247-2250 (see especially note 13); by S. T. Nguyen, L. K. Johnson and R. H. Grubbs in J. Am. Chem. Soc. 1992, 114, 3974-3975 and the supplementary material thereto; by T. Opstal and F. Verpoort in Synlett 2003, 3, 314-320 (see especially reference 16); by M. S. Sanford, M. Ulman and R. H. Grubbs in J. Am. Chem. Soc. 2001, 123, 749-750 (see especially the supplementary material thereto); by A. K. Chatterjee and R. H. Grubbs in Organic Letters 1999, 1(11), 1751-1753; by A. K. Chatterjee, J. P. Morgan, M. Scholl and R. H. Grubbs in J. Am. Chem. Soc. 2000, 122, 3783-3784; and by J. P. Morgan and R. H. Grubbs in Organic Letters 2000, 2(20), 3153-3155 (footnote 13).

Synthesis of the Starting Material

Compounds a) of the formula I, the alkenyl ethers of 2,3,6-trimethylhydroquinone 1-alkanoate, may be obtained e.g. analogeous to the procedure described in EP-A 0 345 593 (see especially reference example 1 on page 6), as described in J. Org. Chem. 1992, 57, 5271-5276 by J. C. Gilbert and M. Pinto (see especially page 5274, right column), as described in Chem. Lett. 1982, 1131-1134 by T. Yoshizawa, H. Toyofuku, K. Tachibana and T. Kuroda or as described in Tetrahedron 2003, 59, 4177-4181 by N. Al-Maharik and N. P. Botting (see especially chapter 3.1.2 and 3.1.6).

The starting material for this synthesis, the 2,3,6-trimethylhydroquinone 1-alkanoates (=4-alkanoyloxy-2,3,5-trimethylphenols) such as 2,3,6-trimethylhydroquinone 1-acetate, may be obtained e.g. by selective hydrolysis of the dialkanoates such as 2,3,5-trimethylhydroquinone diacetate as described in EP 1 239 045.

2,6,10,14-Tetramethylpentadecene may be obtained according to the procedure disclosed of K. Sato, S. Mizuno, M. Hirayama in J. Org. Chem. 1967, 32, 177-180 (see especially page 180).

The phytol derivatives, compounds b) represented by the formula II with $R^4=CH_2R^5$, can be produced by conventional processes for preparing phytyl esters, phytyl silyl ethers and phytyl ethers known to the person skilled in the art. Processes for their manufacture are e.g. described in EP-A 0 004 889 or in FR-A 2 627 384.

The alkenyl ethers of formula I as well as the phytol derivatives of formula II with $R^4=CH_2R^5$ can be used as E/Z-mixture as well as in pure E- or pure Z-form. In both cases preferred is the use of the E/Z-mixtures, since the E/Z ratio of these starting materials is not maintained in the resulting product of formula III and the later following ring closure is independent from this ratio (see FIG. 1).

Cross-Metathesis Reaction

The catalysts, especially those represented by the formulae VIIa, VIIb, VIIc and VIII, can be obtained e. g. according to the processes described in the literature cited above or are also commercially available. Conveniently they are used as solution, whereby as solvent that solvent is used in which the reaction is carried out. The concentration of the solution is not critical. Conveniently the concentration of the solution is from about 0.05% to about 2% by weight, preferably from about 0.1% to about 1% by weight, more preferably from about 0.4% to about 0.6% by weight—based on the total weight of the solution. If the reaction is carried out essentially in the absence of an additional solvent, the catalyst is used as such.

Conveniently the reaction is carried out in the absence or presence of an aprotic organic solvent and essentially in the absence of water and protic (in)organic solvents. Preferably the reaction is carried out essentially in the absence of an additional solvent. Essentially in this context means that the amount of water, protic (in)organic solvents and additional solvent, respectively, is lower than 0.05 mol %, preferably lower than 0.01 mol %, more preferably lower than 0.005 mol %—referred to the total amount of solvent.

If the reaction is carried out in an additional aprotic organic solvent, especially dialkyl ethers $R^{18}$—O—$R^{19}$, wherein $R^{18}$ and $R^{19}$ are independently from each other linear $C_{1-4}$-alkyl or branched $C_{3-8}$-alkyl, $R^{18}$—O—$R^{19}$ preferably being methyl t-butyl ether, diethyl ether or 2,2-dimethylpropyl methyl ether; tetrahydrofuran; tetrahydropyran; 1,4-dioxane; methylene chloride; chloroform; cumene (=iso-propylbenzene) and an optionally once, twice or thrice methylated arylene such as benzene, toluene, 1,2-xylene, 1,3-xylene, 1,4-xylene, mesitylene, pseudocumene, hemellitene or mixtures thereof are used.

More preferably the aprotic organic solvent is tetrahydrofuran, methylene chloride, chloroform, toluene or a mixture thereof. The most preferred aprotic organic solvent is toluene.

The molar ratio of the compound a) of the formula I to the compound b) of the formula II in the reaction mixture conveniently varies from about 1:10 to about 10:1, preferably from about 1:5 to about 5:1, more preferably from about 1:3 to about 1:2.5. Most preferably compound b) is used in excess. If an excess of compound b) of formula II, 2,6,10,14-tetramethylpentadecene or a phytol derivative, is used, non-reacted material can be recycled after termination of the reaction and separation of the product by column chromatography. The same applies if an excess of compound a) is used. In general also a mixture of the non-reacted starting materials, compounds a) and b), can be recycled.

The amount of the cross-metathesis catalyst used, especially of the formulae VIIa, VIIb, VIIc and VIII, is based on the amount of compound a) or b), whichever is used in the lesser molar amount. Usually the relative amount of the catalyst to the amount of compound a) or b), whichever is used in the lesser molar amount, preferably to the amount of compound a) used in the lesser amount, is from about 0.0001 to about 20 mol %, preferably from about 1.0 to about 10 mol %, more preferably from about 2 to about 5 mol %. In this context the expression "amount of catalyst" is to be understood as referring to the amount of the pure catalyst present, even though the catalyst may be impure and/or in the form of an adduct with a solvent.

The amount of the aprotic organic solvent used is conveniently from about 3 to about 15 ml, preferably from about 4 ml to about 10 ml, more preferably from about 4.5 ml to 8 ml, based on 1 mmol of compound a) or b), whichever is used in the lesser amount.

The reaction temperature is dependent from the solvent/solvent mixture used. Conveniently it ranges from about 10° C. to about 120° C., preferably from about 30° C. to about 100° C., more preferably from about 40° C. to about 85° C.

The pressure under which the reaction is carried out is not critical, but dependent from the temperature and the solvent/solvent mixture used. The reaction is conveniently carried out at atmospheric pressure, but when solvents/solvent mixtures with a boiling point below the reaction temperature are used, pressure must be applied. Essentially in the absence of an additional solvent the reaction is carried out preferably at reduced pressure, especially at a pressure below 100 mbar, a pressure below 40 mbar being even more preferred.

Moreover, the process is conveniently carried out under an inert gas atmosphere, preferably gaseous nitrogen or argon.

The process in accordance with the invention can be carried out batchwise or continuously, and in general operationally in a very simple manner, e.g. by adding a mixture of compounds a) and b)—as such or dissolved in the aprotic organic solvent such as mentioned above, preferably as solution—continuously to a mixture of the catalyst and the aprotic organic solvent.

After completion of the addition and an appropriate subsequent reaction period the isolation of the product and its purification if required, can be effected by procedures conventionally used in organic chemistry.

The present invention provides a new route to 4-alkanoyloxy-2,3,5-trimethylphenyl (E/Z)-phytyl ethers (compounds of formula III) and α-tocopheryl alkanoates (compounds of formula V) (see FIG. 1). This process has the advantage of avoiding the production of benzofurans and phytadienes, formed during conventional synthesis of α-tocopherol derivatives and difficult to remove from the product. A further advantage of the process in accordance with the invention is, in addition to the work at lower temperatures compared with conventional α-tocopherol alkanoate production processes, the avoidance of corrosion.

Another aspect of the present invention is a process for the manufacture of α-tocopheryl alkanoates represented by the following formula V

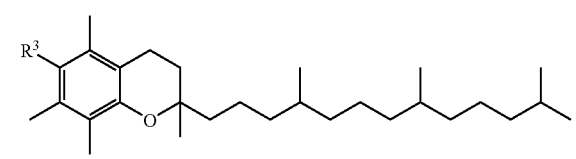

V comprising the following steps:
i) reacting of a compound represented by the following formula I

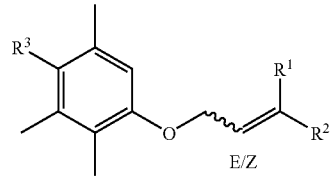

I with a compound represented by the following formula II

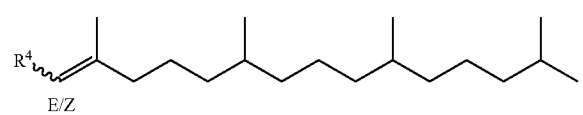

II to a compound represented by the following formula III

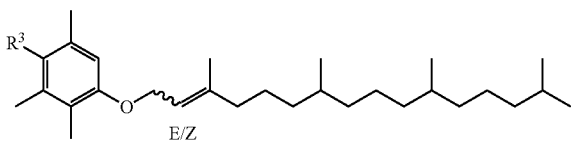

in the presence of a cross-metathesis catalyst, ii) subjecting the compound represented by the formula III and obtained in step i) to a rearrangement to the compound represented by the following formula IV, so-called (E/Z)-1-(5'-alkanoyloxy-2'-hydroxy-3',4',6'-trimethylphenyl)-3,7,11,15-tetramethyl-2-hexadecene ((E/Z)-3-Phytyl-2,5,6-trimethylhydroquinone 1-alkanoate), and

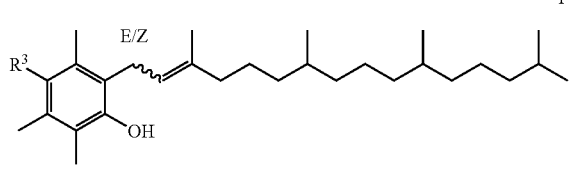

iii) subjecting the compound represented by the formula IV and obtained in step ii) to a cyclization to the compound represented by the formula V, wherein $R^1$, $R^2$, $R^3$ and $R^4$ are as defined above.

While the production of (all-rac)-α-tocopheryl alkanoates (formula V) is preferred, the invention is not limited to the production of that particular isomeric form and other isomeric forms can be obtained by using 2,6,10,14-tetramethylpentadecene or a phytol derivative as the starting material in the appropriate isomeric form. Thus, (RS,R,R)-α-tocopheryl alkanoate will be obtained when using (R,R)-2,6,10,14-tetramethylpentadecene or a (R,R)-phytol derivative.

Step i) is carried out as described above. The steps ii) and iii) are further described in more detail in the following.

Step ii)

The rearrangement in step ii) is a [1,3]-shift. It is suitably performed at temperatures below 20° C., preferably at temperatures from about −30° C. to about −20° C., in the presence of an acidic catalyst.

Acidic catalysts are e.g. Friedel-Crafts catalysts such as boron trifluoride etherate.

The reaction is conveniently carried out in an aprotic organic solvent. Examples are alkanes such as hexane and halogenated alkanes such as carbon tetrachloride or their mixtures. Preferred is a mixture of hexane and carbon tetrachloride.

The pressure under which step ii) is carried out is not critical, but the reaction is conveniently carried out at atmospheric pressure.

Moreover, the process is conveniently carried out under an inert gas atmosphere, preferably gaseous nitrogen or argon.

Step ii) can be carried out batchwise or continuously, and in general operationally in a very simple manner, e.g. by adding the catalyst—as such or suspended in an aprotic organic solvent such as mentioned above—portionwise or continuously to a mixture of the compound of the formula III and the aprotic organic solvent.

After completion of the addition and an appropriate subsequent reaction period the isolation of the product and its purification, which is generally not required, can be effected by procedures conventionally used in organic chemistry.

Step iii)

The ring closure of (E/Z)-1-(5'-alkanoyloxy-2'-hydroxy-3',4',6'-trimethylphenyl)-3,7,11,15-tetramethyl-2-hexadecene (compounds of the formula IV) in accordance with the invention can be effected by their treating with an acid catalyst in the presence or absence of a solvent analogous to the ring closure of (E/Z)-1-(2',5'-dihydroxy-3',4',6'-trimethylphenyl)-3,7,11,15-tetramethyl-2-hexadecene (=(E/Z)-3-phytyl-2,5,6-trimethylhydroquinone) as e.g. described in WO 03/37883, the content of which is incorporated herein.

The following examples illustrate the invention in more detail, but are not intended to limit its scope in any way.

EXAMPLES

The structure of the products was confirmed with $^1$H nuclear magnetic resonance spectroscopy ($^1$H NMR), mass spectroscopy (MS), infrared spectroscopy (IR) and elemental analysis. Their purity was checked with gas chromatography (GC).

Examples A-G

Synthesis of the Starting Material

Example A-1

Synthesis of 4-acetyloxy-2,3,5-trimethylphenyl dimethylallyl ether (Formula I with $R^1=R^2=CH_3$ and $R^3=H_3CC(O)O$)

A schlenk tube equipped with a magnetic stirrer was charged under argon with 450 mg of NaH (10.3-12.2 mmol; in mineral oil 55-65%) and 10 mL of tetrahydrofuran (THF). Then, 1.94 g (10.0 mmol) of 2,3,6-trimethylhydroquinone 1-acetate were added portionwise at 22 to 23° C. while gas evolution was occurring. After 15 minutes 1.7 mL (14.1 mmol) of 3,3-dimethylallyl bromide were added via a syringe and the yellow mixture was stirred overnight at 22 to 23° C. After 18 hours 30 mL of water were added to the reaction mixture and the reaction mixture was extracted thrice with 50 mL of ether. The combined organic phases were then dried over $Na_2SO_4$. After filtration and evaporation of the solvent, the resulting yellow oil was purified by column chromatography over silica gel using a mixture of diethylether and hexane (v/v=1:4) as eluent. 1.82 g of 4-acetyloxy-2,3,5-trimethylphenyl dimethylallyl ether were isolated as a yellow liquid (net yield: 64% based on 2,3,6-trimethylhydroquinone 1-acetate) containing an unknown impurity (ca. 7%). The impurity could be removed by two crystallisations of the raw product in n-hexane at −40° C. to yield pure 4-acetyloxy-2,3,5-trimethylphenyl dimethylallyl ether (purity: 99.9%-GC area).

Example A-2

Alternative Synthesis of 4-acetyloxy-2,3,5-trimethylphenyl dimethylallylether

A schlenk tube equipped with a magnetic stirrer was charged under argon with 10.0 mmol (1.94 g) of 2,3,6-trimethylhydroquinone-1-acetate, 15.0 mmol (1.50 mL) of 3-methyl-2-buten-1-ol, 13.0 mmol (3.410 g) of triphenylphosphine and 100 mL of dry tetrahydrofuran (THF). Then this well stirred solution was cooled to −10° C. to −15° C. and a solution of 16.0 mmol (2.49 mL) of diethyl azodicarboxylate in 8 mL of THF was added over a period of 25 minutes. The resulting yellow solution was stirred at −10° C. to −15° C. for 2 hours and then allowed to warm to 23 to 24° C. After 20 hours, the solution was concentrated in vacuo and the resulting yellow oil was purified by column chromatography over silica gel using a mixture of diethylether and hexane (v/v=1: 4) as eluent. 2.25 g of 4-acetyloxy-2,3,5-trimethylphenyl dimethylallylether were isolated as a yellow oil (net yield: 82.5% based on 2,3,6-trimethylhydroquinone-1-acetate) containing an unknown impurity (ca. 4%).

Example B

Synthesis of (E,Z)-4-acetyloxy-2,3,5-trimethylphenyl 1-butenylether (Formula I with $R^1$=H, $R^2$=$CH_3$ and $R^3$=$H_3CC(O)O$))

A schlenk tube equipped with a magnetic stirrer was charged under argon with 10.3-12.2 mmol (450 mg) of NaH (in mineral oil; 55-65%) and 10 mL of tetrahydrofuran (THF). Then, 10.0 mmol (1.94 g) of 2,3,6-trimethylhydroquinone-1-acetate were added portion-wise at 2 to 3° C. while gas evolution was occurring. After 30 minutes, 14.0 mmol (1.7 mL) of crotyl bromide were added via a syringe and the yellow mixture was stirred at 2 to 3° C. for 1 hour. Then the mixture was allowed to warm up to 23 to 24° C. After 18 hours the mixture was filtered off over a glass frit and the solvent was removed in vacuo. The resulting yellow oil was purified by column chromatography over silica gel using a mixture of diethylether and hexane (v/v=1:4) as eluent. 7.0 mmol (1.74 g) of 4-acetyloxy-2,3,5-trimethylphenyl 1-butenylether were isolated as a colorless oil. (E/Z=89/11; yield: 70% based on 2,3,6-trimethylhydroquinone-1-acetate, purity: 96.4%-GC area).

Example C

Synthesis of 2,6,10,14-tetramethylpentadecene (Formula II with $R^4$=H)

A flask, equipped with a mechanical stirrer and placed under argon, was charged with 1.80 mol (642.6 g) of triphenylmethylphosphonium bromide and 2 L of THF. To this suspension 1.88 mol (1.175 L) of a solution of butyllithium (1.6 mol/L in hexane) were added dropwise during 3 hours at 0° C. The resulting mixture was stirred at 0° C. for an additional hour. Then 1.50 mol (402.7 g) of 6,10,14-trimethyl-2-pentadecanone were added dropwise at 0° C. during 1 hour and the mixture was allowed to warm up to 22 to 23° C. After 2 hours, 150 mL of water were added dropwise and the resulting white suspension was filtered off over decalite. The filtrate was washed thrice with 300 mL of water and dried over $Na_2SO_4$. After filtration and evaporation of the solvent in vacuo, the mixture was filtered off over decalite to remove white cristals and the filtrate was evaporated in vacuo. The resulting crude oil was purified by distillation under vacuum (145° C., 0.2 mbar) to give 1.20 mol (319.2 g) of 2,6,10,14-tetramethylpentadecene as a colorless oil (yield: 80% based on 6,10,14-trimethyl-2-pentadecanone; purity: 96.2%-GC area).

Example D

Synthesis of (E/Z)-(all-rac)-phytyl acetate (Formula II with $R^4$=$CH_2OC(O)CH_3$)

A mixture of 20 mmol (6.23 g) of (E/Z)-(all-rac)-phytol (E/Z ratio=72/28), 25 mmol (1.98 g) of pyridine, 20 mmol (2.04 g) of acetic anhydride and 5 mL of n-hexane was stirred at 21 to 22° C. for 16 to 18 hours. 30 mL of water were added and the resulting mixture was extracted thrice with 50 mL of diethyl ether. The organic phases were combined and washed thrice with 30 mL of aqueous HCl (10% by weight), neutralised with 50 mL of a saturated solution of $NaHCO_3$, washed with 50 mL of a saturated solution of NaCl and with 50 mL of water and dried over $Na_2SO_4$. After filtration, the solvent was removed in vacuo to afford a colorless oil which was purified by column chromatography over silica gel using a mixture of diethylether and hexane (v/v=1:4) as eluent. 5.62 g (16.6 mmol) of (all-rac)-Phytyl acetate were obtained as a colorless oil with an E/Z ratio of 2.5 (yield: 83% based on (all-rac)-phytol).

Example E

Synthesis of (E)-(R,R)-phytyl acetate

Example D was repeated, but instead of (all-rac)-phytol (E)-(R,R)-phytol (E/Z=99.7/0.3) was used. (E)-(R,R)-phytyl acetate (purity: 96.5%-GC area; E/Z=99.6/0.4) was obtained in a yield of 60.5%.

Example F

Synthesis of (E,Z)-(all-rac)-phytyl formiate
(According to EP-A 0 004 889)

(Formula II with $R^4$=$CH_2OC(O)H$)

A mixture of 10 mmol (3.11 g) of (E,Z)-(all-rac)-phytol (E/Z=72/28) and 100 mmol (4.60 g) of formic acid was vigorously stirred at 60° C. for 2.5 hours. Then 30 mL of water were added to the mixture and the organic phase was extracted twice with 30 mL of diethyl ether. The combined organic phases were dried over $Na_2SO_4$ and after filtration, the solvent was removed in vacuo to afford a yellow oil. This oil was purified by column chromatography over silica gel using a mixture of diethylether and hexane (v/v=5:95) as eluent. 9.0 mmol (2.92 g) of (E,Z)-(all-rac)-phytyl formiate were obtained as a colorless oil (E/Z=65/35; yield: 90% based on (all-rac)-phytol).

Example G

Synthesis of (E,Z)-(all-rac)-phytyl benzoate (Formula II with $R^4$=$CH_2OC(O)(phenyl)$)

A mixture of 48.6 mmol (15.02 g) of (E,Z)-(all-rac)-phytol (E/Z=72/28), 51.1 mmol (11.56 g) of benzoic anhydride and 2.4 mmol (0.30 g) of N,N-dimethylaminopyridine in 30 mL of hexane was stirred at 23 to 24° C. for 20 hours. Then 50 ml of water were added and the organic phase was extracted thrice with 50 mL of diethyl ether. The combined organic phases were washed thrice with an aqueous solution of HCl (10% by weight), neutralised with 50 mL of a saturated solution of NaHCO₃, washed with 50 mL of a saturated solution of NaCl and with 50 mL of water and dried over Na₂SO₄. After filtration, the solvent was evaporated in vacuo to afford a colorless oil and a white precipitate. This crude material was purified by column chromatography over silica gel using a mixture of ethyl acetate and hexane (v/v=5:95) as eluent. 37.2 mmol (14.80 g) of (E,Z)-(all-rac)-phytyl benzoate were isolated as a colorless oil (E/Z=68/32; yield: 76% based on (all-rac)-phytol; purity: 99.5%-GC area).

Examples H-Q

Synthesis of 4-acetyloxy-2,3,5-trimethylphenyl (E/Z)-phytyl ethers by Cross-Metathesis Reaction The yield given is the isolated yield measured after purification of the product, 4-acetyloxy-2,3,5-trimethylphenyl (E/Z)-phytyl ether, by column chromatography. The E/Z ratio of the product was determined by $^1$H NMR or high pressure liquid chromatography (HPLC). The E/Z ratio of one starting material, the compound of formula II, was determined by GC. As compound of the formula I 4-acetyloxy-2,3,5-trimethylphenyl dimethylallyl ether was used in examples H-P, in example Q however 4-acetyloxy-2,3,5-trimethylphenyl 1-butenyl ether was used as compound of the formula I. As catalyst was used the Ru-complex represented by formula VIII. The results are summarized in Table 1.

Example H

Synthesis of 4-acetyloxy-2,3,5-trimethylphenyl (E/Z)-phytyl ether Starting from 2,6,10,14-tetramethylpentadecene A schlenk tube, placed under argon and equipped with a magnetic stirrer, was charged with 0.01 mmol (8.4 mg) of the catalyst of formula VIII, 0.2 mmol (36.8 mg) of tridecane and 2 mL of toluene. To this solution a mixture of 0.2 mmol (52.5 mg) of 4-acetyloxy-2,3,5-trimethylphenyl dimethylallyl ether and 0.4 mmol (107 mg) of 2,6,10,14-tetramethylpentadecene dissolved in 4 mL of toluene was added at 21 to 22° C. The resulting brown solution was stirred at 21 to 22° C. for 10 minutes and then at 80° C. for 18 hours. The progress of the reaction can be monitored by GC. After 18 hours the meanwhile orange solution was cooled to 21 to 22° C. and reduced in vacuo to afford a brown oil which was purified by column chromatography over silica gel using a mixture of diethylether and hexane (v/v=1:4) as eluent. 68 mg (0.14 mmol) of 4-acetyloxy-2,3,5-trimethylphenyl (E/Z)-phytyl ether were isolated as a colorless oil (yield: 73% based on 4-acetyloxy-2,3,5-trimethylphenyl dimethylallyl ether) with an E/Z ratio of 2.0 (determined by GC).

TABLE 1

Results of the cross-metathesis reaction of 4-acetyloxy-2,3,5-trimethylphenyl dimethylallyl ether or 4-acetyloxy-2,3,5-trimethylphenyl 1-butenyl ether with compounds of the formula II to 4-acetyloxy-2,3,5-trimethylphenyl (E/Z)-phytyl ether.

| Example | Compound of the formula II | E/Z-ratio of the resulting 4-acetyloxy-2,3,5-trimethylphenyl (E/Z)-phytyl ether | Yield of the resulting 4-acetyloxy-2,3,5-trimethylphenyl (E/Z)-phytyl ether [based on the compound of formula I] |
|---|---|---|---|
| H/I/J | 2,6,10,14-tetramethylpentadecene | 2.0 | 68-73% |
| K | 2,6,10,14-tetramethylpentadecene; no solvent used | 1.8 | 62% |
| L | 2,6,10,14-tetramethylpentadecene; no solvent used, in vacuo (33 mbar) | 2.0 | 83% |
| M | (E/Z)-(all-rac)-phytyl acetate | 2.2 | 59% |
| N | (E)-(R, R)-phytyl acetate | 2.3 | 57% |
| O | (E/Z)-(all-rac)-phytyl formiate | 2.3 | 67% |
| P | (E/Z)-(all-rac)-phytyl benzoate | 1.9 | 58% |
| Q | 2,6,10,14-tetramethylpentadecene | 1.9 | 51% |

Example I

Synthesis of 4-acetyloxy-2,3,5-trimethylphenyl (E/Z)-phytyl ether Starting from 2,6,10,14-tetramethylpentadecene Example H was repeated under the same conditions except that instead of 0.01 mmol 0.02 mmol of the catalyst of formula VIII were used. The yield was 68% based on 4-acetyloxy-2,3,5-trimethylphenyl dimethylallyl ether.

Example J

Synthesis of 4-acetyloxy-2,3,5-trimethylphenyl (E/Z)-phytyl ether Starting from 2,6,10,14-tetramethylpentadecene Example H was repeated by using the fourfold amount of reactants. The yield was 68% based on 4-acetyloxy-2,3,5-trimethylphenyl dimethylallyl ether.

Example K

Synthesis of 4-acetyloxy-2,3,5-trimethylphenyl (E/Z)-phytyl ether Starting from 2,6,10,14-tetramethylpentadecene in the Absence of Solvent A mixture of 0.8 mmol of 4-acetyloxy-2,3,5-trimethylphenyl dimethylallylether, 1.6 mmol of 2,6,10,14-tetramethylpentadecene and 0.04 mmol of the catalyst was vigorously stirred at 80° C. for 16 hours. The yield was 62% based on 4-acetyloxy-2,3,5-trimethylphenyl dimethylallyl ether. The E/Z ratio of the product, 4-acetyloxy-2,3,5-trimethylphenyl (E/Z)-phytyl ether, was 1.8.

Example L

Synthesis of 4-acetyloxy-2,3,5-trimethylphenyl (E/Z)-phytyl ether Starting from 2,6,10,14-tetramethylpentadecene in the Absence of Solvent in Vacuo A mixture of 0.8 mmol of 4-acetyloxy-2,3,5-trimethylphenyl dimethylallylether, 1.6 mmol of 2,6,10,14-tetramethylpentadecene and 0.04 mmol of the catalyst was vigorously stirred at 80° C. for 2 hours in vacuo (33 mbar). The yield was 83% based on 4-acetyloxy-2,3,5-trimethylphenyl dimethylallyl ether. The E/Z ratio of the product, 4-acetyloxy-2,3,5-trimethylphenyl (E/Z)-phytyl ether, was 2.0.

Example M

Synthesis of 4-acetyloxy-2,3,5-trimethylphenyl (E/Z)-phytyl ether Starting from (E/Z)-(all-rac)-phytyl acetate Example H was repeated under the same conditions except that instead of 0.4 mmol of 2,6,10,14-tetramethylpentadecene 0.4 mmol of (E/Z)-(all-rac)-phytyl acetate (E/Z=2.5) were used. The yield was 59% based on 4-acetyloxy-2,3,5-trimethylphenyl dimethylallyl ether. The E/Z ratio of the product, 4-acetyloxy-2,3,5-trimethylphenyl (E/Z)-phytyl ether, was 2.2.

Example N

Synthesis of 4-acetyloxy-2,3,5-trimethylphenyl (E/Z)-phytyl ether Starting from (E)-(R,R)-phytyl acetate Example H was repeated under the same conditions except that instead of 0.4 mmol of 2,6,10,14-tetramethylpentadecene 0.4 mmol of (E)-(R,R)-phytyl acetate (E/Z=99.7/0.3) were used. The yield was 57% based on 4-acetyloxy-2,3,5-trimethylphenyl dimethylallyl ether. The E/Z ratio of the product, 4-acetyloxy-2,3,5-trimethylphenyl (E/Z)-phytyl ether, was 2.3.

Example O

Synthesis of 4-acetyloxy-2,3,5-trimethylphenyl (E,Z)-phytyl ether Starting from (E,Z)-(all-rac)-phytyl formiate Example H was repeated under the same conditions except that instead of 0.4 mmol of 2,6,10,14-tetramethylpentadecene 0.4 mmol of (E,Z)-(all-rac)-phytyl formiate (E/Z=65/35) were used. The yield was 67% based on 4-acetyloxy-2,3,5-trimethylphenyl dimethylallylether. The E/Z ratio of the product, 4-acetyloxy-2,3,5-trimethylphenyl (E,Z)-phytyl ether, was 2.3.

Example P

Synthesis of 4-acetyloxy-2,3,5-trimethylphenyl (E,Z)-phytyl ether Starting from (E,Z)-(all-rac)-phytyl benzoate Example H was repeated under the same conditions except that instead of 0.4 mmol of 2,6,10,14-tetramethylpentadecene 0.4 mmol of (E,Z)-(all-rac)-phytyl benzoate (E/Z=68/32) were used. The yield was 58% based on 4-acetyloxy-2,3,5-trimethylphenyl dimethylallylether. The E/Z ratio of the product, 4-acetyloxy-2,3,5-trimethylphenyl (E,Z)-phytyl ether, was 1.9.

Example Q

Synthesis of 4-acetyloxy-2,3,5-trimethylphenyl (E,Z)-phytyl ether Starting from 2,6,10,14-tetramethylpentadecene and (E,Z)-4-acetyloxy-2,3,5-trimethylphenyl 1-butenylether Example H was repeated under the same conditions except that instead of 0.2 mmol of 4-acetyloxy-2,3,5-trimethylphenyl dimethylallylether 0.2 mmol of (E,Z)-4-acetyloxy-2,3,5-trimethylphenyl 1-butenylether (E/Z=89/11) were used. The yield was 51% based on (E,Z)-4-acetyloxy-2,3,5-trimethylphenyl 1-butenylether. The E/Z ratio of the product, 4-acetyloxy-2,3,5-trimethylphenyl (E,Z)-phytyl ether, was 1.9.

The invention claimed is:

1. A process for the manufacture of compounds represented by the following formula III

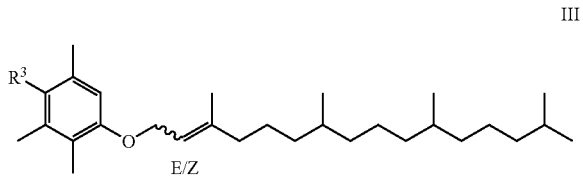

wherein R3 is C2-5-alkanoyloxy,
by the reaction of
a) a compound represented by the following formula I

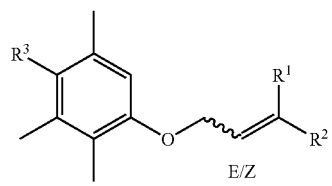

wherein R' and R2 are independently from each other H or C1-5-alkyl, with the proviso that at least one of R1 and R2 is not H, and
wherein R3 is as defined above, with
b) a compound represented by the following formula II

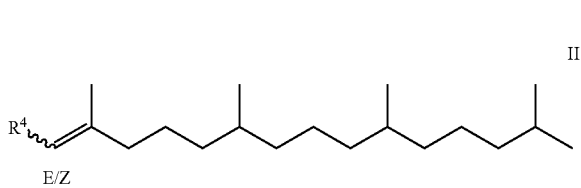

wherein R4 is H or CH2—R5,
wherein R5 is formyloxy, C2-5-alkanoyloxy, benzoyloxy, C1-5-alkoxy or OSiR6R7R8,
wherein R6, R7 and R8 are independently from each other C1-6-alkyl or phenyl,
in the presence of a cross-metathesis catalyst, wherein the cross-metathesis catalyst is

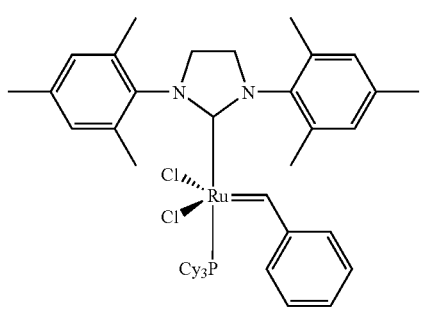

wherein Cy is cyclohexyl.

2. The process as claimed in claim 1, wherein the reaction is carried out in an aprotic organic solvent.

3. The process as claimed in claim 2, wherein the aprotic organic solvent is a dialkyl ether R18-O—R19, tetrahydrofuran, tetrahydropyran, 1,4-dioxane, methylene chloride, chloroform, cumene, an optionally once, twice or thrice methylated arylene, or a mixture thereof,
wherein R18 and R19 are independently from each other linear C1-4-alkyl or branched C3-8-alkyl.

4. The process as claimed in claim 3, wherein the aprotic organic solvent is tetrahydrofuran, methylene chloride, chloroform, toluene or a mixture thereof.

5. The process as claimed in claim 2, wherein from about 3 ml to about 15 ml of the aprotic organic solvent are used per mmol of compound a) or b), whichever is used in the lesser amount.

6. The process as claimed in claim 1, wherein the reaction is carried out essentially in the absence of an additional solvent.

7. The process as claimed in claim 6, wherein the reaction is carried out in vacuo.

8. The process as claimed in claim 1, wherein the relative amount of the cross-metathesis catalyst to the amount of compound a) or b), whichever is used in the lesser amount, is from about 0.0001 mol % to about 20 mol %.

9. The process according to claim 1, wherein the molar ratio of compound a) to compound b) present in the reaction mixture is from about 1:10 to about 10:1.

10. The process as claimed in claim 1 wherein the reaction is carried out at temperatures from about 10° C. to about 120° C.

11. A process for the manufacture of α-tocopheryl alkanoates represented by the following formula V

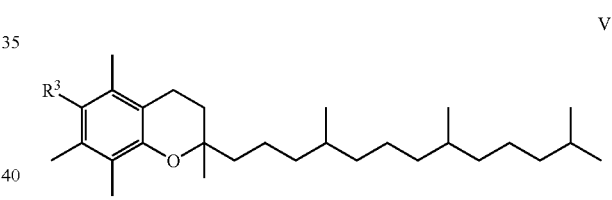

comprising the following steps:
i) reacting of a compound represented by the following formula I

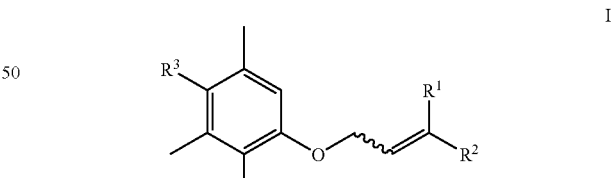

with a compound represented by the following formula II

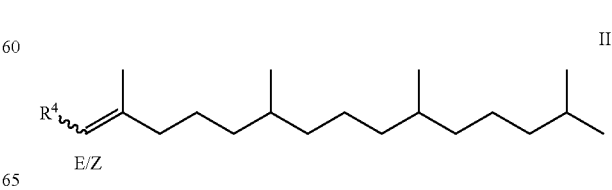

to a compound represented by the following formula III

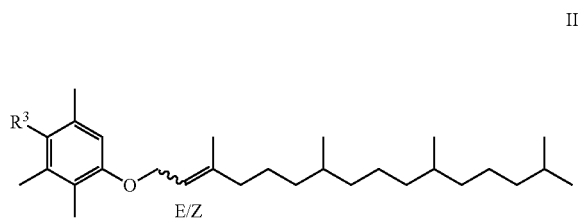

in the presence of a cross-metathesis catalyst, ii) subjecting the compound represented by the formula III and obtained in step i) to a rearrangement to the compound represented by the following formula IV, and

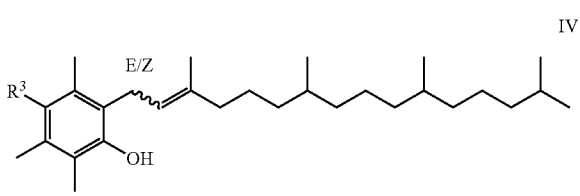

iii) subjecting the compound represented by the formula IV and obtained in step ii) to a cyclization to the compound represented by the formula V, wherein R1, R2, R3 and R4 are as defined in claim 1, wherein the cross-metathesis catalyst is

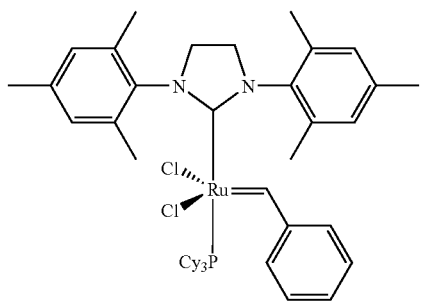

and wherein Cy is cyclohexyl.

12. Compounds of the formula III

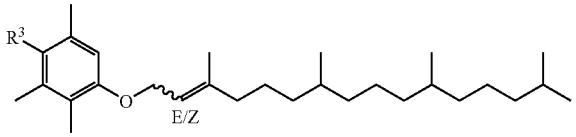

wherein R3 is C2-5-alkanoyloxy.

13. Compounds of the formula IX

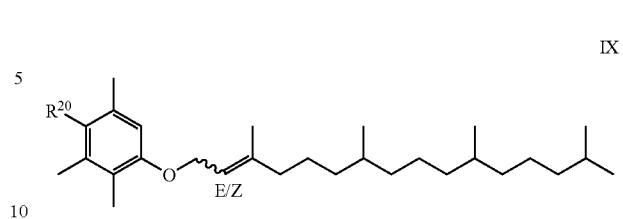

wherein R20 is C3-5-alkanoyloxy.

14. The process as claimed in claim 3, wherein the aprotic organic solvent is toluene.

15. The process as claimed in claim 2, wherein from about 4 ml to about 10 ml of the aprotic organic solvent are used per mmol of compound a) or b), whichever is used in the lesser amount.

16. The process as claimed in claim 2, wherein from about 4.5 ml to about 8 ml of the aprotic organic solvent are used per mmol of compound a) or b), whichever is used in the lesser amount.

17. The process as claimed in claim 6, wherein the reaction is carried out at a pressure below 100 mbar.

18. The process as claimed in claim 1, wherein the relative amount of the cross-metathesis catalyst to the amount of compound a) or b), whichever is used in the lesser amount, is from about 1.0 mol % to about 10 mol %.

19. The process as claimed in claim 1, wherein the relative amount of the cross-metathesis catalyst to the amount of compound a) or b), whichever is used in the lesser amount, is from about 2 to about 5 mol %.

20. The process according to claim 1, wherein the molar ratio of compound a) to compound b) present in the reaction mixture is from about 1:5 to about 5:1.

21. The process according to claim 1, wherein the molar ratio of compound a) to compound b) present in the reaction mixture is from about 1:3 to about 1:2.5.

22. The process as claimed in claim 1 wherein the reaction is carried out at temperatures from about 30° C. to about 100° C.

23. The process as claimed in claim 1 wherein the reaction is carried out at temperatures from about 40° C. to about 85° C.

* * * * *